(12) United States Patent
Meunier et al.

(10) Patent No.: US 9,393,189 B2
(45) Date of Patent: Jul. 19, 2016

(54) PROCESS OF PREPARING A CROSSLINKED GEL

(75) Inventors: Stephane Meunier, Thoiry (FR); Francois Bourdon, Gaillard (FR)

(73) Assignee: TEOXANE, Geneva (CH)

( * ) Notice: Subject to any disclaimer, the term of this patent is extended or adjusted under 35 U.S.C. 154(b) by 153 days.

(21) Appl. No.: 13/989,197

(22) PCT Filed: Dec. 6, 2011

(86) PCT No.: PCT/IB2011/055495
§ 371 (c)(1),
(2), (4) Date: May 23, 2013

(87) PCT Pub. No.: WO2012/077054
PCT Pub. Date: Jun. 14, 2012

(65) Prior Publication Data
US 2013/0237615 A1 Sep. 12, 2013

(30) Foreign Application Priority Data
Dec. 6, 2010 (FR) ...................................... 10 60135

(51) Int. Cl.
| | |
|---|---|
| *A61K 8/73* | (2006.01) |
| *A61Q 19/08* | (2006.01) |
| *C08G 59/00* | (2006.01) |
| *C08B 37/00* | (2006.01) |
| *C08B 37/08* | (2006.01) |
| *C08J 3/075* | (2006.01) |

(52) U.S. Cl.
CPC ............... *A61K 8/735* (2013.01); *C08B 37/00* (2013.01); *C08B 37/0072* (2013.01); *C08G 59/00* (2013.01); *C08J 3/075* (2013.01); *A61K 2800/91* (2013.01); *A61Q 19/08* (2013.01); *C08J 2305/08* (2013.01)

(58) Field of Classification Search
None
See application file for complete search history.

(56) References Cited

U.S. PATENT DOCUMENTS

| | | | |
|---|---|---|---|
| 8,052,990 | B2 | 11/2011 | Hermitte et al. |
| 2003/0094719 | A1 | 5/2003 | Yang et al. |
| 2004/0127698 | A1 | 7/2004 | Tsai et al. |

(Continued)

FOREIGN PATENT DOCUMENTS

| | | |
|---|---|---|
| EP | 1 818 344 A1 | 8/2007 |
| FR | 2 865 737 | 8/2005 |

(Continued)

OTHER PUBLICATIONS

Mar. 2, 2012 International Search Report issued in International Application No. PCT/IB2011/055495.

(Continued)

*Primary Examiner* — Bethany Barham
*Assistant Examiner* — Dominic Lazaro
(74) *Attorney, Agent, or Firm* — Shumaker, Loop & Kendrick, LLP

(57) ABSTRACT

The subject of the present invention is a process of preparing a crosslinked gel of at least one polysaccharide or one of its salts, including at least the steps consisting in: a) providing, at a temperature below 35° C., an aqueous gel including at least one polysaccharide in an uncrosslinked form together with at least one difunctional or multifunctional epoxy crosslinking agent; b) maintaining the mixture of step a) at a temperature below 35° C. for at least one hour; c) stimulating the crosslinking reaction of the mixture obtained after step b), and if need be; d) recovering said crosslinked gel formed.

16 Claims, 3 Drawing Sheets

(56) References Cited

U.S. PATENT DOCUMENTS

| | | | |
|---|---|---|---|
| 2005/0281880 A1* | 12/2005 | Wang | 424/486 |
| 2006/0105022 A1 | 5/2006 | Yokokawa et al. | |
| 2007/0036745 A1 | 2/2007 | Leshchiner et al. | |
| 2008/0139796 A1 | 6/2008 | Yagi et al. | |
| 2010/0021544 A1 | 1/2010 | Bourges et al. | |
| 2010/0303873 A1* | 12/2010 | Piron et al. | 424/401 |

FOREIGN PATENT DOCUMENTS

| | | |
|---|---|---|
| FR | 2 908 775 | 5/2008 |
| WO | WO 00/46252 | 8/2000 |
| WO | WO 2006/056204 A1 | 6/2006 |
| WO | WO 2009/071697 A1 | 6/2009 |

OTHER PUBLICATIONS

Mar. 2, 2012 Written Opinion of the International Search Authority issued in International Application No. PCT/IB2011/055495.

Jul. 21, 2011 Preliminary Search Report issued in French Application No. 1060135 (with translation).

Jul. 21, 2011 Written Opinion of the Patentability of the Invention issued in French Application No. 1060135 (with translation).

* cited by examiner

PROCESS OF PREPARING A CROSSLINKED GEL

The object of the present invention is to provide a process of preparing hydrogels based on a crosslinked polysaccharide, and preferably based on hyaluronic acid, or one of its salts.

BACKGROUND OF THE INVENTION

Naturally present, in the skin, hyaluronic acid is known for its viscoelastic properties and also for its very great propensity to absorb water. Its properties largely explain the elasticity of skin. Its biocompatibility, tolerance and lack of toxicity are such that, for more than a decade, this molecule has had applications in the medical and cosmetic fields, and in particular for filling wrinkles. Thus, the injection of a crosslinked polysaccharide hydrogel into the dermis at the wrinkles to be treated helps to lessen, or even eliminate, the local sag in the structure of the dermis that is a wrinkle.

In general, the polysaccharide and more particularly hyaluronic acid, is used in a crosslinked form owing to the greater resistance in this particular form to degradation and to heat.

These crosslinked polysaccharide gels may be obtained by various methods of preparation. These methods generally require two main steps, the first consisting in hydrating the polysaccharide in question, to convert it into an aqueous gel, and the second aiming to crosslink said aqueous gel in the presence of an agent typical of causing the crosslinking thereof.

Conventional crosslinking methods for hyaluronic acid are usually carried out at a temperature of around 40° C., or even 50° C., for a time of less than 3 hours, thereby making it possible for the polysaccharide gel to be crosslinked satisfactorily. It is for this reason that tins method of preparation is widely used in the industry.

As illustrations of these processes, the processes described in US 2006/0105022, which comprises the use of a mixture comprising at least 10% hyaluronic acid, a crosslinking agent and water under acid or basic conditions. In WO 2006/056204, which comprises a step of treating the crosslinked hyaluronic acid gel with divinyl sulphone and in US 2007/0036745, which results in a cohesive gel starting from a hyaluronane polymer crosslinked with divinyl sulphone (DVS) may especially be mentioned.

For obvious reasons, it is a constant objective to improve the mechanical properties of the hydrogels for applications in the medical and cosmetic fields.

BRIEF SUMMARY OF THE INVENTION

The aim of the present invention is specifically to provide a process for obtaining crosslinked gels having particularly advantageous mechanical properties.

Against all expectation, the inventors have found that a novel method of preparing crosslinked gels enables the properties of said gels to be significantly improved in comparison with the properties manifested by those obtained by means of a conventional process.

DETAILED DESCRIPTION OF THE INVENTION

Thus, the present invention relates, according to a first of its aspects, to a process of preparing a crosslinked gel of at least one polysaccharide or one of its salts, comprising at least the steps consisting in:

a) providing, at a temperature below 35° C., an aqueous gel comprising at least one polysaccharide in an uncrosslinked form together with at least one difunctional or multifunctional epoxy crosslinking agent;
b) maintaining the mixture of step a) at a temperature below 35° C. for at least one hour;
c) stimulating the crosslinking reaction of the mixture obtained after step b), and if need be;
d) recovering said crosslinked gel formed.

More precisely, the invention relates from the unexpected observation fey the inventors that the use of two different crosslinking rates one after the other, the first being particularly slow and the second significantly more rapid, makes it possible to obtain crosslinked polysaccharide gels having viscoelastic properties that are significantly improved in comparison with those gels obtained by means of conventional processes employing a single crosslinking rate.

As is apparent from Example 3 below, the novel viscoelastic properties manifested by the crosslinked gels obtained via the implementation of a process of the invention can in no way be reproduced with a gel obtained according to a conventional crosslinking process, that is to say employing, for carrying out said crosslinking reaction, a single rate applied at a temperature above 40° C., even when this single reaction rate is applied for prolonged periods of time.

According to one particular embodiment a process of the invention may furthermore include a step e) of stopping the crosslinking, consisting in exposing the crosslinked gel to conditions propitious for stopping the crosslinking thereof, this step possibly being earned out before, during or after the recovery step d).

According to a preferred embodiment, step e) is earned out before step d).

Advantageously, the crosslinked gel obtained after implementing a process according to the invention is a single-phase gel and more particularly a predominantly elastic viscoelastic gel, that is to say with little or even no ability to flow in the absence of stresses other than its own weight.

According to another aspect of the present invention, this relates to the use of a crosslinked gel obtained by implementing a process as defined above for the lasting filling of volume defects of the skin, and especially the filling of wrinkles.

I) Process

A process of the invention comprises, in a first step, providing an aqueous gel comprising at least one polysaccharide in an uncrosslinked form together with a difunctional or multifunctional epoxy crosslinking agent.

The term "uncrosslinked" is understood in the context of the present invention to mean an aqueous polysaccharide gel which is not crosslinked or slightly crosslinked, that is to say a gel having a phase-shift angle δ, measured under dynamic rheology conditions at 1 Hz, that is greater than 40° when subjected to a stress above 1 Pa.

More precisely, the aqueous gel considered in step a) may be obtained beforehand by bringing together, in an appropriate receptacle:

(i) an aqueous medium;
(ii) at least, one polysaccharide, or one of its salts, in an uncrosslinked form; and
(iii) at least one difunctional or multifunctional epoxy crosslinking agent, and by homogenizing the mixture thus obtained, the order of addition of said compounds ii), (ii) and (iii) into the receptacle being indifferent.

According to a first embodiment variant this aqueous gel may be formed by introducing, into the receptacle, the aqueous medium and the polysaccharide, the mixture thus formed being simultaneously and/or subsequently homogenized, and then, by adding the crosslinking agent with simultaneous and/or subsequent homogenization.

According to a second embodiment variant, this aqueous gel may be obtained by introducing, into the receptacle, the aqueous medium, the polysaccharide and the crosslinking agent, with the mixture thus formed being homogenized simultaneously and/or subsequently.

This second embodiment variant is advantageous in that a single homogenization step is carried out.

Advantageously, this step of forming the aqueous gel may be carried out at a temperature below 35° C., preferably at a temperature ranging from 15 to 25° C., and better still at room temperature.

Whatever the embodiment in question, the formation of an aqueous gel as considered in step a) involves at least one homogenization operation.

The purpose of this operation, whether or not carried out in the presence of the crosslinking agent, is more particularly for the polysaccharide in the aqueous medium and, if need be, the crosslinking agent, to be hydrated and homogenized perfectly and thus to help to optimize the properties of the crosslinked gel expected.

For these reasons, the homogeneity of the crosslinked gel is closely dependent on the homogeneity of the gel before crosslinking.

The homogenization is considered to be satisfactory when the solution obtained is uniformly coloured, with no agglomerates, and has a uniform viscosity. The homogenization may advantageously be carried out under mild operating conditions so as to prevent degradation of the polysaccharide chains.

This step is more important when the polysaccharide has a high molecular weight, because the hydration of such a compound tends to result in the formation of a high-viscosity solution within which the appearance of agglomerates is commonly observed.

The duration of this homogenization step depends on the nature of the polysaccharide, and more particularly the molecular weight and the concentration thereof, on the operation conditions within the aqueous medium and the homogenizing device used.

Adjusting the homogenization time suitable for obtaining a sufficiently homogeneous aqueous polysaccharide gel falls within the general knowledge of a person skilled in die art.

Preferably, a homogenization step according to the present invention may take place over a time of less than 200 minutes, preferably less than 150 minutes, or even between 15 and 100 minutes.

As follows from the foregoing, two different crosslinking rates are applied, one after another, to the aqueous gel of step a), these being illustrated by steps b) and c) of the process of the invention respectively.

The purpose of the crosslinking is to create bridges between the polysaccharide chains, and especially the hyaluronic acid chains, making it possible to obtain a dense solid three-dimensional network from a viscous solution.

i) Conditions for Carrying Out Step b)

Step b) entails keeping the mixture of step a) at a temperature below 35° C. for a time of at least one hour.

Thus, step b), under the environmental conditions in which it is carried out, is compatible only with a slow crosslinking rate.

Preferably, step b) is carried out at a temperature ranging from 15 to 25° C., and better still at room temperature.

The slow crosslinking rate considered in step b) may especially be characterized by the rate of disappearance, within the mixture obtained after step a), of the epoxy crosslinking agent.

Thus the average rate of disappearance of the epoxy crosslinking agent during step b) is less than 5 ppm/min, preferably less than 2 ppm/min, for a hyaluronic acid concentration of 20 mg/g.

Preferably, step b) takes place at a time of longer than one hour, preferably longer than two hours.

Preferably, step b) may be carried out over a time ranging from 1 to 2 hours 30 minutes, and better still from 1 hour 30 minutes to 2 hours.

ii) Conditions for Carrying Out Step c)

Step c) entails however the stimulation of the crosslinking reaction.

Thus, the term "stimulation" is understood to mean, in the context of the present invention, a significant, increase in tire rate of the crosslinking reaction.

The particular conditions to be adopted in order to stimulate the crosslinking reaction may depend on the nature of the polysaccharide, on its molecular weight, on the aqueous medium and on the nature of the crosslinking agent.

In general, this stimulation may be achieved by bringing the mixture obtained after step b) into contact with a triggering element, or stimulant, such as, for example by heating or exposure to UV, or even by bringing said mixture into contact with a material of the catalyst type.

The choice of such a triggering element falls within the general knowledge of a person skilled in the art.

Thus, a triggering element may be applied by:
 immersion of the receptacle comprising the mixture obtained after step b) into a bath containing a hot fluid;
 exposure of said mixture to radiation of certain wavelengths, for example in the UV, or to microwave or even infrared radiation;
 irradiation by means of ionizing rays, as per the process described in document US 2008/0139796; and
 enzymatic crosslinking.

In the context of the present invention, this triggering element is advantageously represented by an increase in temperature imposed on the mixture obtained after step b).

A particularly suitable temperature for step c) depends on the nature of the polysaccharide in question.

If the polysaccharide is hyaluronic acid, a particularly suitable temperature for step c) is between 35° C. and 60° C., preferably between 45 and 55° C., and better still between 48 and 52° C.

In the case of step b) described above, the rapid crosslinking rate considered in step c) may in particular be characterized by the rate of disappearance, within the mixture obtained after step b), of the epoxy crosslinking agent.

Thus, the mean rate of disappearance of the crosslinking agent during step c) is greater than 5 ppm/min, preferably greater than 7 ppm/min, for a hyaluronic acid concentration of 20 mg/g.

The degree of crosslinking also depends on the crosslinking time imposed on the mixture obtained after step b). The longer the time, the higher the degree of crosslinking, with however an optimum not to be exceeded without running the risk of degrading the polysaccharide.

Thus, step c) may be carried out over a time ranging from 30 to 300 minutes, preferably 100 to 200 minutes, and better still 150 to 190 minutes.

Advantageously, the crosslinking conditions are adjusted so as to maximize the crosslinking efficiency, that is to say to obtain a maximum effective degree of crosslinking for a minimum amount of crosslinking agent used.

According to one particularly preferred embodiment, crosslinking steps b) and c) are carried out in basic medium, the receptacle containing the mixture obtained after step a) being maintained for one hour at room temperature and then placed in a thermostatted bath heated to a temperature of around 50 to 55° C., for a time of at least 1 hour, and preferably of between 1 hour 30 minutes and 3 hours 30 minutes.

As explained above, stopping the crosslinking (step e)) may be carried out before, during or after step d) of recovering the gel.

Such a step, in a process according to the invention, requires exposing the crosslinked gel or, during crosslinking, even the receptacle containing it, to conditions propitious for stopping the crosslinking or else to conditions capable of stopping the formation of bonds between the various polysaccharide chains.

According to a preferred embodiment variant, step e) is carried out before step d).

For example, with regard to the thermal conditions that will be applied to stimulate the crosslinking process, the crosslinking may be stopped:
by simply removing the receptacle from the thermostatted bath and cooling it until it returns to room temperature;
by placing the receptacle in a bath of cold water, preferably at a temperature below room temperature, until the temperature, within said receptacle is close to room temperature; or even
by extracting the gel from said receptacle.

In the case of radiation crosslinking, this is stopped by stopping the exposure of said gel to the radiation.

According to one particular embodiment, a process of the invention may further include at least one step consisting in making the mixture obtained after step a), or even obtained after step b), pass through at least one device capable of retaining any particle with a diameter greater than 100 microns.

This specific step, also called in the rest of the description "extrusion step", thus takes place after step a) and before step b) and/or after step b) and before step c).

As will emerge from the examples below, the advantageous effect associated with this extrusion step is that a crosslinked gel having further improved viscoelastic properties is obtained.

Choosing the type of extrusion device falls within the general knowledge of a person skilled in the art.

Advantageously, the extrusion step is carried out by using at least one device comprising at least one filter.

A person skilled in the art is capable of defining the suitable characteristics in terms of porosity, geometry, strength and retention capability of such a filter so that the latter lets through the mixture obtained after step a), or even after step b), while retaining any particles with a diameter greater than 100 microns.

In the rest of the present description, the device comprising at least one filter used for carrying out the extrusion step may also be denoted by the expression "extrusion device".

Advantageously, the extrusion step is carried out by means of at least one device comprising at least one filter having a porosity ranging from 2 to 100 microns, preferably from 5 to 50 microns, better still 8 to 30 microns, and more particularly 10 microns.

Advantageously, the linear rate of extrusion of the mixture obtained after step a) and/or b) through the extrusion device(s) is slow so as not to degrade the polysaccharide chains during their passage therethrough.

Thus, the linear rate of extrusion of said mixture(s) obtained after step a) and/or step b) through the extrusion device(s) is between 1 and 100 cm/min, preferably between 1 and 4 cm/min.

According to yet another particular embodiment, the process of the invention may be carried out at least partly within a specific receptacle having a deformable wall, such as, for example, a pouch.

This is because the deformability properties of such a receptacle and its hermeticity make it possible to carry out the various steps of a process of the invention, and especially the homogenization and crosslinking steps, under optimal conditions that result in an even better crosslinked gel being obtained, that is to say one having injectability properties superior to those displayed by a gel obtained according to a process employing a conventional receptacle of the pot or tank type.

The crosslinked gel obtained after the process of the invention as described above, cannot in general be injected directly, in particular because of its high polysaccharide concentration and/or of the possible presence of crosslinking agent residues or else because of its physiological and/or pH conditions incompatible with use in the fields of applications considered above.

Furthermore, the gel obtained after the process of the invention may especially have too high a stiffness to be injected as such into a patient.

Therefore, several additional steps, known to those skilled in the art, can be carried out to obtain an injectable hydrogel.

More particularly, a step of neutralizing and expanding this gel is required in order to give it its implant qualities. The chains of the polysaccharide network are then stretched and hydrated, while the pH is brought to that of the dermis.

A step of protecting and redensifying the gel can also be carried out for further improving the qualities of the implant, according to the know-how of a person skilled in the art. The gel must be physiologically formulated by virtue of the presence of salts in equivalent amounts to those of the medium injected.

For even higher purity, an additional purification step may also be carried out.

Finally, the hydrogel thus obtained may be used to fill syringes under controlled atmosphere conditions, said syringes then possibly undergoing a sterilization step, preferably a thermal sterilization step.

II) Polysaccharide

The term "polysaccharide" is understood to mean any polymer consisting of several monosaccharides linked together by glycoside bonds and having the general formula: —[$C_x(H_2O)_y$)]$_n$—.

A polysaccharide according to the invention is more particularly selected with regard to the properties that it is desired to see the crosslinked gel obtained according to the invention display. More particularly such a polysaccharide must have good biocompatibility.

Thus, a physiologically acceptable polysaccharide or polysaccharide salt may be of natural or synthetic origin.

The polysaccharides suitable for the invention may especially be chosen from the following: chondroitin sulphate, keratan, keratan sulphate, heparin, heparin sulphate, xanthan, carrageenan, hyaluronic acid, chitosan, cellulose and derivatives thereof, alginate, starch, dextran, pullulan, galactomannan and biologically acceptable salts thereof.

The polysaccharide salts in accordance with the invention are more particularly chosen from physiologically acceptable salts such as the sodium salt, the potassium salt, the zinc salt, the silver salt and mixtures thereof, preferably the sodium salt.

Preferably, a polysaccharide or polysaccharide salt according to the invention has a high molecular weight, preferably a molecular weight greater than or equal to 100 000 Da, better still greater than or equal to 1 MDa (or $1.10^6$ Da), or even greater than 3 MDa (or $3.10^6$ Da), depending on the application in question.

One particularly preferred polysaccharide is hyaluronic acid or one of its salts, preferably sodium hyaluronate (NaHA).

Advantageously, the polysaccharide may be present within the aqueous gel of said polysaccharide in a noncrosslinked form in a content ranging from 5 to 15% by weight, preferably in a content greater than 10% by weight, relative to the total weight of said aqueous gel.

As mentioned above, the mixing of step a) of the process according to the invention results in at least one aqueous polysaccharide gel in an uncrosslinked form, or one of its salts, being combined with at least one epoxy crosslinking agent.

Now, said aqueous polysaccharide gel may itself result from bringing beforehand said polysaccharide, or one of its salts, into contact with an aqueous medium.

The term "aqueous medium" is understood in the context of the present invention to mean any liquid medium containing water and having the property of dissolving a polysaccharide or one of its salts.

The nature of the aqueous medium is more particularly dependant on the type of crosslinking envisaged, but also on the type of polymer used.

In this regard, a suitable aqueous medium may be either acid or basic.

One particularly preferred aqueous medium is an alkaline medium, preferably sodium hydroxide (NaOH), more particularly a sodium hydroxide solution having a pH greater than 12.

III) Epoxy Crosslinking Agent

The term "crosslinking agent" is understood to mean any compound capable of inducing crosslinking between the various polysaccharide chains.

The choice of this crosslinking agent, for the polysaccharide to be crosslinked clearly falls within the competence of a person skilled in the art.

A crosslinking agent in accordance with the invention is chosen from difunctional or multifunctional epoxy crosslinking agents, such as butanediol diglycidyl ether (BDDE), diepoxyoctane or 1,2-bis(2,3-epoxypropyl)-2,3-ethylene, and mixtures thereof.

Preferably, a crosslinking agent according to the invention is butanediol diglycidyl ether.

Adjusting the amount of crosslinking agent to carry out the crosslinking reaction also falls within the competence of a person skilled in the art.

According to one particularly preferred embodiment, the process according to the invention uses sodium hyaluronate in alkaline medium with butanediol diglycidyl ether as crosslinking agent.

Throughout the description, including the claims, the expression "comprising a" should be understood as being synonymous with "comprising at least one" unless specifically stated otherwise.

The expressions "between . . . and . . . " and "ranging from . . . to . . . " should be understood to mean that the limits are inclusive, unless specified otherwise.

The following examples and figures are presented by way of non-limiting illustration of the invention.

EXAMPLES

Example 1

For each of the crosslinked gels described below, 10 g of hyaluronic acid (1.5 MDa), 73 g of 1% sodium hydroxide and 1.2 g of butanediol diglycidyl ether (BDDE) were employed.

The particular conditions applied for each gel were the following:

Product A (Control)

The preparation protocol was as follows:

1. homogenization at room temperature of the hyaluronic acid/1% sodium hydroxide mixture for about 1 hour 30 minutes in order to obtain a perfectly homogeneous viscous solution;

2. addition of the crosslinking agent (BDDE) and further homogenization at room temperature for about 20 minutes;

3. incubation of the hyaluronic acid/1% sodium hydroxide mixture/BDDE viscous solution for 3 hours at 52° C.; and 4. neutralization, swelling and homogenization of the solid obtained (crosslinked hyaluronic acid solution) in an acidified phosphate buffer solution so as to obtain a hydrogel containing 20 mg/g of hyaluronic acid with a pH close to neutrality.

Product B (According to the Invention)

The protocol was the same as that described for product A but carried out with, between steps 2 and 3, an intermediate step during which the mixture obtained after step 2 was maintained at room temperature for 2 hours.

This intermediate step may also be denoted, in the rest of the present description, by the expression "rest step".

The total "hyaluronic acid/BDDE" contact time before incubation at 52° C. was therefore about 2 hours 20 minutes.

Product C (According to the Invention)

The protocol was fee same as that described for product A but carried out, after step 2 of adding BDDE and homogenizing for 15 minutes, with an extrusion step followed by the intermediate step, in which the product B was maintained for 2 hours at room temperature, and then the incubation step 3 at 52° C. for 3 hours.

This extrusion step was carried out by means of a circular screen of the extruder screen pack type, having a 10 micron mesh size.

The total hyaluronic acid/BDDE contact time before incubation at 52° C. was again about 2 hours 20 minutes.

Syringes were all filled with products A, B and C. The viscoelastic properties of these three products were measured using a rheometer (Haake RS6000) with a cone/plate geometry (1° cone angle/35 mm diameter plate). A strain scan was carried out and the elastic modulus G' (in Pa) and the phase-skill angle δ (in °) were measured for a stress of 5 Pa.

Results

Figure 1:
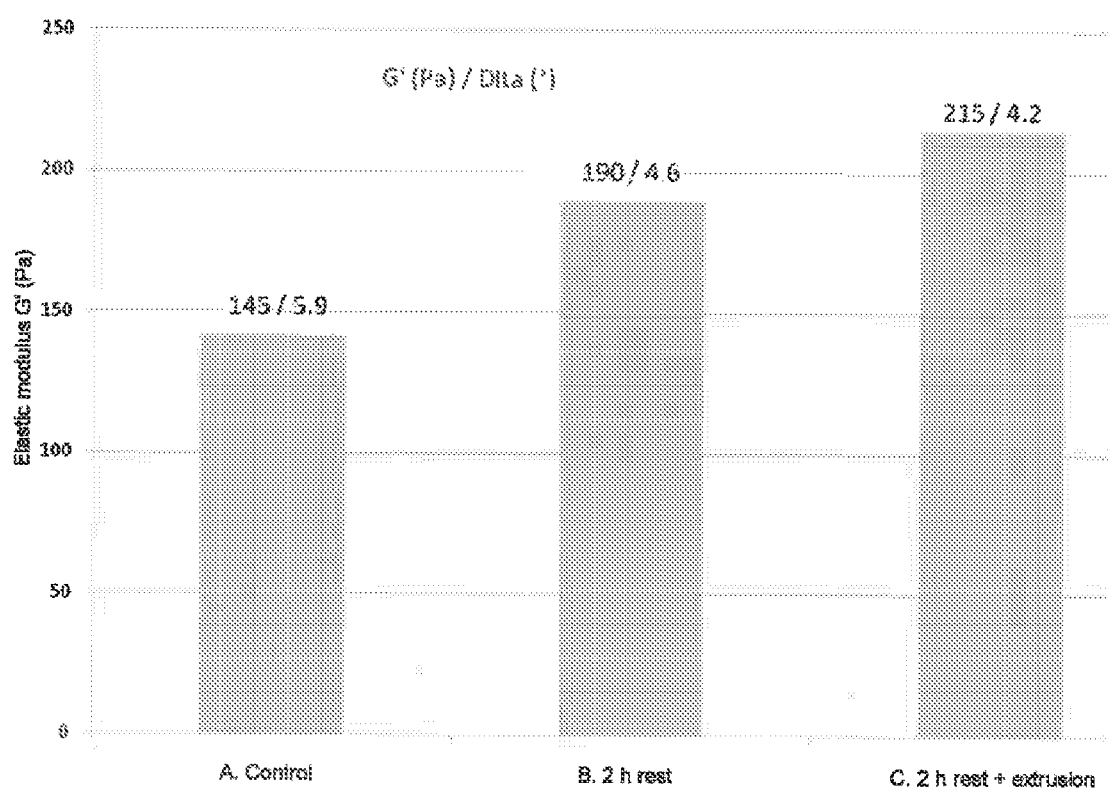
FIG. 1: illustrates the viscoelastic properties of hyaluronic add gels measured by their elastic modulus G' (in Pa).

FIG. 1 below shows the measured elastic modulus G' values (in PA). For indication, the value of the phase-shift angle δ is indicated (in °) at the top of each column, to the right of the G' value.

The measured phase shift is extremely small, which means that these gels exhibit a mainly elastic character.

The results of FIG. 1, and especially that of product B, show a significant increase in G' when the crosslinking reaction is carried out via a process of the invention, that is to say by employing two different rates for carrying out the crosslinking reaction, one alter another.

This effect is even more pronounced when an extrusion step is carried out by using a device comprising a filter of 10 micron porosity.

Example 2

Evaluation, at various stages, of the amount of crosslinking agent in a hyaluronic acid gel subjected to a process according to the invention.

Several crosslinked hydrogels were prepared in parallel using a process of the invention via the use of a specific receptacle, namely a deformable pouch as defined above.

A 12% hyaluronic acid solution in 1% NaOH was thus prepared. After hydrating the hyaluronic acid, a BDDE solution diluted five-fold in 1% NaOH was added.

The total amount of BDDE used therefore corresponded to a theoretical content equivalent to 1.8 mg/g in a 20 mg/g hyaluronic acid hydrogel.

Several fractions A, B and C were then prepared from the mixture obtained above.

Fraction A corresponds to a hyaluronic acid gel maintained for 1 hour at room temperature (RT) before the incubation step described below.

Fraction B corresponds to a hyaluronic acid gel maintained for 2 hours at room temperature before the incubation step described below.

Finally, Fraction C corresponded to a hyaluronic acid gel maintained for 1 hour at room, temperature before the incubation step described below, this rest step being furthermore combined with a step of extrusion through a screen of 10 µm mesh size.

After the various treatments described above, fractions A, B and C were incubated at 52° C. for 3 hours.

The solids respectively obtained after this incubation step (crosslinked hyaluronic acid solutions) were then neutralized, swelled and homogenized in a 7.3 pH phosphate buffer solution so as to obtain a 20 mg/g hyaluronic acid hydrogel.

To monitor the amount of crosslinking agent consumed at various steps of the process of the invention, a BDDE analysis was carried out at various steps.

Thus, samples T1 and T2 correspond to gel samples taken after maintaining, prior to the incubation step for 3 hours at 52° C., the hyaluronic acid/BDDE mixtures at room temperature for 1 and 2 hours respectively.

The samples T1 and T2 then underwent the same neutralization, swelling and homogenization steps as those described above for fractions A, B and C, so as to obtain 20 mg/g hyaluronic acid hydrogels.

The samples A, B and C corresponded to gel samples taken from the corresponding fractions after incubation for 3 hours at 52° C. and conversion to a 20 mg/g hydrogel.

Results

Table 1 shows the measured amounts of crosslinking agent and the elastic modulus (G' in Pa) values of the hydrogels obtained.

For indication, values of the complex viscosity |η|* and the phase-shift angle δ are also mentioned.

TABLE 1

| Samples: | BBDE (mg/g) | G' (Pa) | \|η\|* (Pa · s) | δ (°) |
|---|---|---|---|---|
| T1 | 1.53 | NCO*(predominantly viscous solutions of low elasticity owing to the absence of crosslinking, δ > 45°) | | |
| T2 | 1.43 | | | |
| Fraction A (maintained at RT for 1 h) | 0.20 | 136 | 22 | 5 |
| Fraction B (maintained at RT for 2 h) | 0.17 | 174 | 28 | 5 |
| Fraction C (maintained at RT for 1 h, and an extrusion step through a 10 µm filter) | 0.20 | 159 | 25 | 5 |

*NCO = not carried out.

It should be noted that the measured residual BDDE contents correspond to non-sterilized and non-purified gels.

The measured contents of crosslinking agent (BDDE) in samples T1 and T2 are of the same order of magnitude. The small reduction in BDDE content observed compared with the theoretical content indicated above is explained by a slow rate of the crosslinking reaction, as the case may be, associated with the degradation of the BDDE because of the instability of the epoxy functional groups.

In contrast, the reduction in BDDE content is greatly accentuated after the 52° C. incubation step for 3 hours, this substantial consumption of BDDE thus corresponding to a rapid rate of the crosslinking reaction.

In respect of the mechanical properties of the gels obtained (fractions A, B and C), it is worthwhile pointing out that (i) the measured phase shift is extremely small, meaning that these gels have mainly an elastic character, (ii) the highest elastic modulus G' is obtained for the gel resulting from fraction B, that is to say with a step of maintaining at room temperature for 2 hours before incubation at 52° C. and (iii) traction C, extruded before crosslinking, has a significantly increased elastic modulus G' in comparison with the same hydrogel but not extruded (fraction A).

Points (ii) and (iii) above thus corroborate the advantageous effects due to using two different crosslinking rates, one after another, for the crosslinking reaction but also due to the extrusion step in the context of a process for preparing a crosslinked gel according to the invention.

Example 3

An aqueous polysaccharide gel/crosslinking agent mixture identical to that described in Example 2 above was prepared.

Two tests were then carried out:

In the first case, several fractions A, B, C and D were prepared from the above mixture. The crosslinking reaction was carried out by leaving said fractions for 2 hours at room temperature before placing them at 52° C. for various times.

In the second case, several fractions A', B', C' and D' were also prepared. Unlike fractions A, B, C and D, these were directly incubated at 52° C. for various times.

The incubation tunes at 52° C. for the various fractions considered were the following:
Fractions A and A': 2 hours 40 minutes
Fractious B and B': 2 hours 50 minutes
Fractions C and C': 3 hours
Fractions D and D': 3 hours 10 minutes.

The crosslinked hyaluronic acid gels obtained after the incubation steps were then neutralized, then swelled and homogenized in a 7.3 pH phosphate buffer (PB) solution so as to obtain 20 mg/g hyaluronic acid hydrogels. The following characterizations and analyses were carried out on the hydrogels thus obtained.

Results

Table 2 below gives the values of the elastic moduli G' (in Pa) of the hydrogels obtained. For indication, the value of the complex viscosity |f|* and the phase-shift angle δ are also given.

TABLE 2

| | Amplitude scan (cone/plate) τ = 5 Pa | | |
|---|---|---|---|
| | G' (Pa) | |η| * (Pa · s) | δ (°) |
| A  | 174.5 | 27.9 | 5.1 |
| B  | 186.9 | 29.9 | 5.7 |
| C  | 174.0 | 27.8 | 5.5 |
| D  | 152.2 | 24.3 | 4.8 |
| A' | 119.2 | 19.1 | 7.1 |
| B' | 126.5 | 20.3 | 6.4 |
| C' | 125.8 | 20.1 | 6.3 |
| D' | 122.7 | 19.6 | 5.7 |

Figure 2:
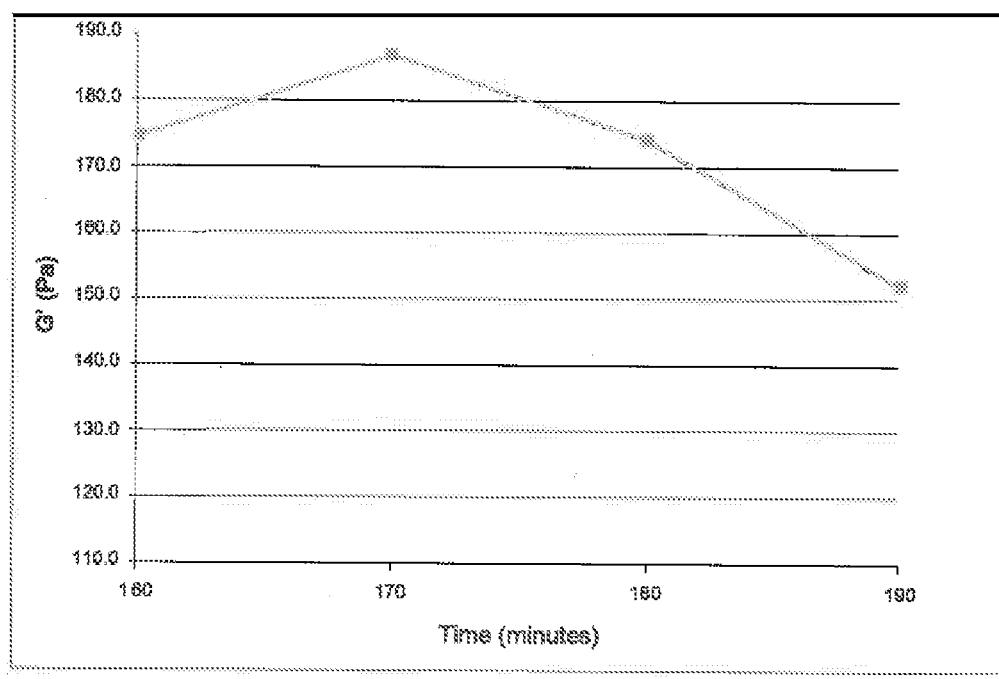
FIG. 2: illustrates the variation in elastic modulus G' (in Pa) of hydrogels obtained after a crosslinking step characterized by a first step of maintaining a mixture of a 12% aqueous hyaluronic acid gel with BDDE for two hours at room temperature followed by a second step of incubating said mixture at 52° C. for various times.
Figure 3:
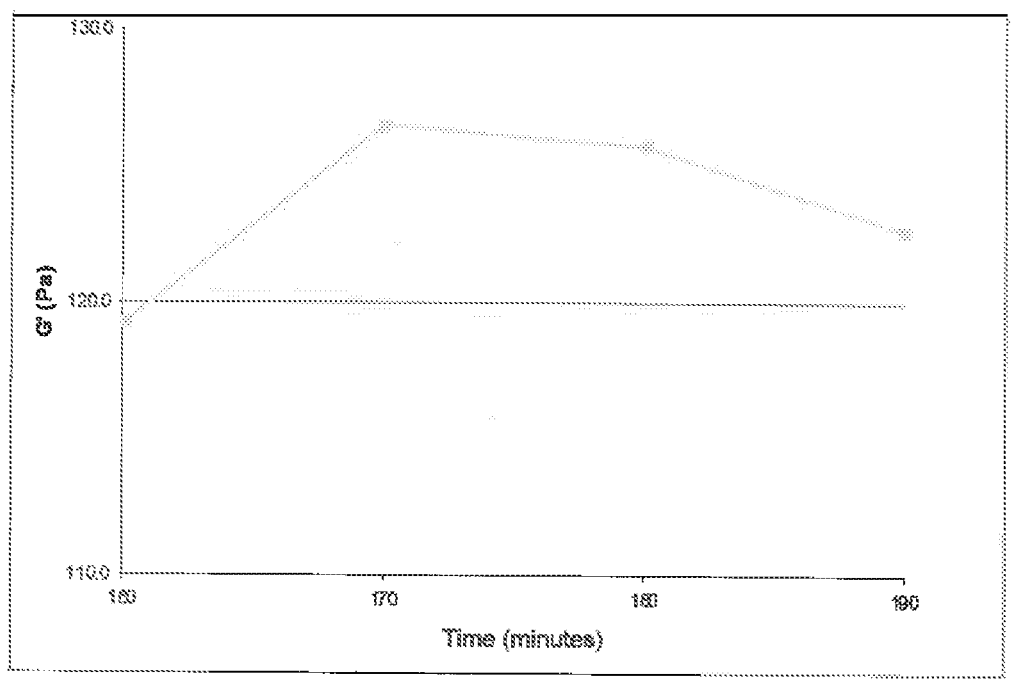
FIG. 3: illustrates the variation in the elastic modulus G' (in Pa) of hydrogels obtained after a crosslinking step characterized by a single step of incubating a mixture of a 12% aqueous hyaluronic acid gel with BDDE at 52° C. for various times.

FIGS. 2 and 3 below illustrate the results given in Table 2 above.

The optimum effectiveness of the 52° C. incubation step on the crosslinking therefore occurs at about 3 hours with or without the prior step of maintaining the aqueous polysaccharide gel/crosslinking agent mixture at room temperature.

The hydrogels obtained by a process employing a maintenance step at room temperature for 2 hours, before tire 52° C. incubation step, have viscoelastic properties that are significantly better than the maximum values observed for the hydrogels obtained by a protocol with the step of maintaining at room temperature being absent.

These results demonstrate that the beneficial effect due to the presence, for carrying out the crosslinking reaction, of a step of maintaining an aqueous polysaccharide gel/crosslinking agent mixture at ambient temperature for a long time cannot be simply reproduced by extending the crosslinking time at 52° C.

It is because the optimum G' measured on the hydrogels obtained according to a crosslinking process of fee invention has never been achieved by the hydrogels obtained according to a conventional crosslinking process, whatever the duration of the incubation step at 52° C.

What is claimed is:

1. A process of preparing a crosslinked gel of at least one polysaccharide or one of its salts, comprising:
   a) providing, at a temperature between 15° C. and below 35° C., an aqueous mixture resulting from mixing at least one polysaccharide or salt thereof in an uncrosslinked form at least one difunctional or multifunctional epoxy crosslinking agent and an aqueous medium;
   b) homogenizing, at a temperature between 15° C. and 35° C., the aqueous mixture obtained in step a), until a homogeneous gel is obtained; and
   c) after step b), performing a resting step in which the homogeneous gel obtained in step b) is rested at a temperature between 15° C. and 35° C. for at least one hour to initiate a first crosslinking rate, and
   d) after step c), incubating the mixture of step c) at a temperature between 45° C. and 55° C. for 30 minutes to 300 minutes to initiate a second crosslinking rate.

2. The process according to claim 1, wherein the polysaccharide is hyaluronic acid or one of its salts.

3. The process according to claim 1, wherein steps a) and b) are carried out at a temperature ranging from 15 to 25° C.

4. The process according to claim 1, wherein the first crosslinking of step c) is carried out for a time ranging from 1 hour to 2.5 hours.

5. The process according to claim 1, wherein the first crosslinking of step c) is carried out for a time ranging from 1.5 hours to 2 hours.

6. The process according to claim 1, wherein the step b) comprises at least one homogenization step which takes place for a time of less than 200 minutes.

7. The process according to claim 1, wherein the epoxy crosslinking agent is butanediol diglycidyl ether (BDDE), diepoxyoctane, 1,2-bis(2,3-epoxypropyl)-2,3-ethylene, or a mixture thereof.

8. The process according to claim 1, wherein the polysaccharide has a molecular weight greater than or equal to 1 MDa.

9. The process according to claim 1, wherein the polysaccharide is present within the aqueous gel of said polysaccharide in a noncrosslinked form in a content of between 5 and 15% by weight, relative to the total weight of said aqueous gel.

10. The process according to claim 1, wherein it employs sodium hyaluronate in alkaline medium and butanediol diglycidyl ether (BDDE), as crosslinking agent.

11. The process according to claim 1, wherein the crosslinked gel is a predominantly elastic viscoelastic single-phase gel.

12. The process according to claim 1, wherein the polysaccharide or salt thereof is selected from the group consisting of chondroitin, heparin, xanthan, carrageenan, chitosan, cellulose, alginate, starch, dextran, pullulan, galactomannan, biologically acceptable salts thereof, and a mixture thereof.

13. The process according to claim 12, wherein the polysaccharide salt is selected from the group consisting of a sodium salt of a polysaccharide, potassium salt of a polysaccharide, zinc salt of a polysaccharide, silver salt of a polysaccharide, and a mixture thereof.

14. The process according to claim 1, further comprising recovering the crosslinked gel formed.

15. The process according to claim 7, wherein the epoxy crosslinking agent is butanediol diglycidyl ether (BDDE).

16. The process according to claim 1, further comprising extruding the homogeneous gel obtained in step b), prior to step c).

* * * * *